(12) United States Patent
Hällgren

(10) Patent No.: US 6,432,937 B1
(45) Date of Patent: Aug. 13, 2002

(54) TREATMENT FOR JOINT INFLAMMATION

(75) Inventor: Roger Hällgren, Dragontorpsvägen (SE)

(73) Assignee: Astra Aktiebolag, Södertälje (SE)

( * ) Notice: Subject to any disclaimer, the term of this patent is extended or adjusted under 35 U.S.C. 154(b) by 0 days.

(21) Appl. No.: 09/011,623

(22) PCT Filed: Dec. 16, 1997

(86) PCT No.: PCT/SE97/02124

§ 371 (c)(1),
(2), (4) Date: Feb. 12, 1998

(87) PCT Pub. No.: WO98/27987

PCT Pub. Date: Jul. 2, 1998

(30) Foreign Application Priority Data

Dec. 20, 1996 (SE) .............................................. 9604751

(51) Int. Cl.$^7$ .......................... A61K 31/58; A61K 31/56
(52) U.S. Cl. ....................................... 514/174; 514/179
(58) Field of Search ................................. 514/178, 174

(56) References Cited

U.S. PATENT DOCUMENTS

| | | | | |
|---|---|---|---|---|
| 5,482,934 A | * | 1/1996 | Calatayud et al. ........... | 514/174 |
| 5,840,332 A | * | 11/1998 | Lerner et al. ................ | 424/646 |
| 5,889,049 A | * | 3/1999 | Juergens ..................... | 514/510 |

FOREIGN PATENT DOCUMENTS

| EP | 0 502 092 B1 | 7/1995 | ............ A61K/9/22 |
|---|---|---|---|
| SE | 0502092 | 7/1995 | ............ A61K/9/22 |

OTHER PUBLICATIONS

T.H.J. Florin et al., "Is the Arthritis of Crohn's Disease Due to Intestinal Disease," Abstract of the 4$^{th}$ United, European Gastroenterology Week, Sep. 17–21, 1995, Berlin, Germany.

Jiri Mestecky et al., "Mucosal Immunity in the Female Genital Tract: Relevance to Vaccination Efforts against the Human Immunodeficiency Virus," Aids Research and Human Retroviruses, vol. 10, Supplement 2, 1994, pp. S11–S20.

Thomas B. Tomasi, "Introduction: An Overview of the Mucosal System," Handbook of Mucosal Immunology, 1994, pp. 3–8.

Per Brandtzaeg, "Basic Mechanisms of Mucosal Immunity—A Major Adaptive Defense System," The Immunologist, 3/3 (1995), pp. 89–96.

Journal of Computer Assisted Tomography, vol. 20, No. 4, 1996, Matthias Bollow et al., "CT–Guided Intraarticular Corticosteroid Injection into the Sacroiliac Joints in Patients with Spondyloarthropathy: Indication and Follow–Up with Contrast–Enhanced MRI", pp. 512–521.

Journal of rheumatology, vol. 22, No. 9, 1995, Daniel J. McCarty et al., "Treatment of Rheumatoid Joint Inflammation with Intrasynovial Triamcinolone Hexacetonide", pp. 1631–1635.

The Journal of Rheumatology, vol. 10, No. 3, 1983, Gary D. Sladek et al., "Beclomethasone dipropionate in the treatment of the rheumatoid larynx", pp. 518–519.

* cited by examiner

Primary Examiner—Theodore J. Criares
(74) Attorney, Agent, or Firm—Fish & Richardson P.C.

(57) ABSTRACT

The invention provides the use of a glucocorticoid substance which has a minimal systemic effect in the manufacture of a medicament for oral or rectal administration for non-topical use in the treatment of joint inflammation.

15 Claims, No Drawings

TREATMENT FOR JOINT INFLAMMATION

This is a International Patent Application No. PCT/SE97/02124, with an international filing date of Dec. 16, 1997, now pending.

FIELD OF THE INVENTION

The present invention provides a new treatment for joint inflammation.

BACKGROUND TO THE INVENTION

The symptoms of joint inflammation are generally associated with spondyloarthropathies (for example ankylosing spondylitis, psoriatic arthropathy, reactive arthritides and sacroiliitis) and rheumatoid arthritis. The joint inflammation is localised to different joints in these different conditions. In ankylosing spondylitis the inflammation is localised to the spine, the sacroiliac joints, and also often to the peripheral large joints (e.g. the knees, elbows and ankles). In sacroiliitis the inflammation is isolated to the sacroiliac joints but sometimes occurs in the peripheral joints as well. The other spondyloarthropathies have a similar clinical picture so far as which joints are inflamed. In rheumatoid arthritis a symmetrical joint inflammation occurs.

Rheumatoid arthritis and the spondyloarthropathies have in common a chronic inflammation of the synovial and extrasynovial structures such as the tendons and ligaments. The inflammatory reaction of the joints is dominated by certain inflammatory cells (for example neutrophils, activated lymphocytes and macrophages) which all contribute to the joint pain and the destruction of the joints.

The drugs which have in the past been used to treat joint inflammation are based on symptomatic anti-inflammatory treatments or disease modifying treatments. The dominating drugs for symptomatic treatments are non-steroidal anti-inflammatory drugs, orally active glucocorticosteroids with a mainly systemic effect or intraarticular injections of glucocorticosteroids. The disease modifying treatments include drugs which, by influencing the immune reactions of the body, reduce joint inflammation. Examples of disease modifying drugs include methotrexate, azathioprine, gold salts, cyclophosphamide and sulphasalazine. All of these treatments unfortunately cause severe side effects and are not particularly effective. For example glucocorticoid administration is generally directed against the local inflammation, i.e. it has been used to treat directly the inflammatory cells present in the joint inflammation. The routes used to administer such glucocorticoid treatment results in severe side effects on the body including effects on the skeleton and muscles.

It has now surprisingly been found that oral or rectal administration of a glucocorticoid substance which has a minimal systemic effect is effective in controlling the joint inflammation.

SUMMARY OF THE INVENTION

According to the invention there is provided the use of a glucocorticoid substance which has a minimal systemic effect in the manufacture of a medicament for oral or rectal administration for non-topical use in the treatment of joint inflammation.

According to the invention there is further provided a method of treating a human or non-human mammal suffering from joint inflammation which comprises administering non-topically and orally or rectally to the human or non-human mammal a therapeutically effective amount of a glucocorticoid substance which has a minimal systemic effect.

According to the invention there is also provided a pharmaceutical composition comprising a glucocorticoid substance which has a minimal systemic effect in association with a pharmaceutically acceptable diluent, adjuvant or carrier, which composition is for non-topical use in the treatment of joint inflammation.

DETAILED DESCRIPTION OF THE INVENTION

The invention is preferably used to treat a human or non-human mammal who suffers from rheumatoid arthritis, peripheral oligoarthritis, peripheral arthropathies or spondyloarthropathy, especially ankylosing spondylitis, psoriatic arthropathy, reactive arthritides and sacroiliitis. It can also be used to treat human or non-human mammals suffering from conditions where the joint inflammation is associated with intestinal inflammation.

The non-human mammals which the invention can be used to treat include domestic mammals such as cats, dogs, horses, sheep and cows.

The glucocorticoid substance used in the present invention is preferably one which has a first pass metabolism of at least 90%. The first pass metabolism of a glucocorticoid substance may be measured using the method described by Andersson, P et al in Xenobiotica (1987) 17: 35–44.

More preferably the glucocorticoid substance is budesonide, rofleponide or a derivative thereof, belcomethasone dipropionate, beclomethasone monopropionate, ciclesonide, tipredane, flunisolide, triamcinolone acetonide or fluticasone propionate. Budesonide is particularly preferred.

The glucocorticoid substance is used non-topically and can be administered either orally or rectally. When administered orally, it is administered oesophageally, generally in the form of tablets, pills, capsules, syrups, powders or granules; when administered rectally, it is optionally in the form of suppositories or enemas.

It may be administered on its own or as a pharmaceutical composition in association with a pharmaceutically acceptable diluent, adjuvant or carrier. Particularly preferred are compositions not containing material capable of causing an adverse, e.g. an allergic reaction.

The glucocorticoid substance may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, and/or paraffin, and then compressed into tablets. If coated tablets are required, the cores, prepared as described above, may be coated with a concentrated sugar solution which may contain e.g. gum arabic, gelatine, talcum, and/or titanium dioxide. Alternatively, the tablet may be coated with a suitable polymer dissolved in a readily volatile organic solvent. The tablet preferably has an enteric coating to allow release of the glucocorticoid substance in the lower intestine. Suitable capsules may be prepared by using the methods described in EP-A-502092, WO 95/08323 or WO 97/27843.

For the preparation of soft gelatine capsules, glucocorticoid substance may be admixed with e.g. a vegetable oil or polyethylene glycol. Hard gelatine capsules may contain granules of the substance using either the above mentioned excipients for tablets, e.g. lactose, saccharose, sorbitol, mannitol, starches, cellulose derivatives or gelatine. Also liquid or semisolid formulations of the substance may be filled into hard gelatine capsules.

Liquid preparations for oral application may be in the form of syrups or suspensions, for example solutions containing the glucocorticoid substance, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

Rectal enema formulations can be in the form of simple suspensions of the glucocorticoid substance in a pharmaceutically acceptable carrier or may be in the form of a rectal foam formulation, for example as described in EP-A-468555.

The glucocorticoid substance is preferably administered at a dosage of from 0.1 to 40 mg, more preferably from 0.5 to 20 mg, most preferably from 1 to 10 mg, either as a single dose or in divided doses from 2 to 4 times per day. The pharmaceutical composition for oral administration used in the present invention should preferably be prepared in such a way that the glucocorticoid substance is released in the lower part of the small intestine or the upper part of the large intestine. Preferably the composition should be prepared so that the substance is released in the lower third of the small intestine or the upper fourth of the large intestine.

The invention is illustrated by the following examples where budesonide is administered orally using the Entocort™ preparation as described in EP-A-502092.

EXAMPLE 1

A 36 year old man who had been suffering from sacroiliitis and peripheral oligoarthritis for over 7 years had previously been treated with various anti-inflammatory and disease-modifying drugs (for example non-steroidal anti-inflammatory drugs, prednisolone and methotrexate) without success.

Before commencement of the treatment he had a swollen left knee and ankle, clinical signs of inflamed sacroiliac joints and had been unable to work for 8 months. His initial morning stiffness rating, joint index, spinal movement and joint pain are shown in Table 1.

He was initially treated with 9 mg of budesonide once a day for the first four weeks and then the dose was reduced to 6 mg per day. The results after 2 months of the treatment are shown in Table 1. Two months after withdrawal of the treatment according to the invention his condition deteriorated.

TABLE 1

| Test | Before | After |
| --- | --- | --- |
| Morning stiffness/min | 120 | 20 |
| Joint arthritic index | 127 | 0 |
| Spinal movement/cm | 1 | 4 |
| Joint pains: at rest/in motion | 5/9.5 | 1.5/1.5 |

The normal value of morning stiffness is 0 min. The joint arthritic index was measured using the Lansbury index whose normal value is 0. The spinal movement was measured using Shober's Test whose normal value is from 5 to 6 cm. The joint pain at rest and in motion was estimated using a VAS (visual analogue scale) where 0 represents no pain and 10 very severe pain.

EXAMPLE 2

A 43 year old man who had suffered from ankylosing spondylitis for 12 years had previously been treated with non-steroidal anti-inflammatory drugs and disease-modifying drugs, for example sulphasalazine and methotrexate, without success. Initially his left knee, both ankles, and both sternoclavicular and sacroiliac joints were clinically inflamed and he had the symptoms indicated in Table 2.

He was treated with 9 mg of budesonide once a day and one month after the start of the treatment he experienced a marked improvement in his symptoms as can be seen from Table 2. One month after the total withdrawal of the treatment his condition had returned to how it was before the treatment had started.

TABLE 2

| Test | Before | After |
| --- | --- | --- |
| Morning stiffness/min | 270 | 0 |
| Joint arthritic index | 127 | 80 |
| Spinal movement/cm | 2.5 | 3.5 |
| Joint pains: at rest/in motion | 8/8 | 1/1.7 |
| ESR rate/mm/h | 85 | 30 |
| C-reactive protein/(mg/l) | 140 | 25 |

The tests were carried out in the same way as in Example 1 except that the laboratory inflammatory activity was measured using the ESR (erythrocyte sedimentation rate) whose normal value is less than 5 mm/h and the C-reactive protein plasma concentration which is usually less than 10 mg/litre.

EXAMPLE 3

A 71 year old woman who had developed small joint inflammation of the hands and feet 18 months previously initially had a symmetric inflammation of both wrists, all finger joints and the ankles. She was diagnosed as having rheumatoid arthritis.

She was treated with 9 mg of budesonide once a day. Her initial symptoms and after 4 months of treatment are shown in Table 3.

TABLE 3

| Test | Before | After |
| --- | --- | --- |
| Morning stiffness/min | 180 | 0 |
| Joint arthritic index | 205 | 0 |
| ESR rate/mm/h | 70 | 16 |
| C-reactive protein/(mg/l) | 41 | 10 |

The tests for the symptoms were carried out in the same way as in Examples 1 and 2.

EXAMPLE 4

A male patient, 47 year old, who had previously been healthy and without any joint complaints, developed an arthritic reaction in both ankles and the midtarsal joints of both feet. Gradually he developed also an inflammation of the left knee joint and tendinitis of both Achilles tendons. He was treated with non-steroid anti-inflammatory drugs and prednisolone with some relief of the joint pains. At admittance to hospital four months later, the diagnosis was established as a HLA-B27 associated reactive arthritis. After treatment with 9 mg of budesonide once a day for three weeks, he had no tendinitis of the Achilles tendons and he experienced a marked improvement in his symptoms as can be seen from Table 4.

TABLE 4

| Test | Before | After |
|---|---|---|
| Morning stiffness/min | 120 | 60 |
| Joint arthritic index | 112 | 6 |
| Ritchie index | 9 | 4 | wherein the Ritchie index is an alternative joint arthritic index.

EXAMPLE 5

A 22 year old male patient had suffered from a HLA-B27 associated sacroiliitis with peripheral arthropathies for 8 years. He had previously been treated with different drugs: methotrexate, sulphasalazine, gold salts and prednisolone without any apparent disease-modifying effect. At admittance to the hospital he suffered from direct pains of the sacroiliac joints and inflammation of the left knee and left ankle. The sacroiliac radiogram showed sacroiliitis. After 2 weeks treatment with 9 mg of budesonide per day he started to improve and at clinical follow up 6 weeks after start of treatment with budesonide his condition was considerably improved as can be seen from Table 5.

TABLE 5

| Test | Before | After |
|---|---|---|
| Morning stiffness/min | 180 | 0 |
| Joint arthritic index | 127 | 0 |
| Ritchie index | 3 | 0 |
| Joint pains: at rest/in motion | 9.5/8 | 0/0 |

EXAMPLE 6

A 48 year old male patient had for 10 months suffered from diffuse joint pains and morning stiffness. His condition deteriorated and he was admitted to hospital. He had prominent symmetric synovial inflammations of finger joints (metacarpophalangeal joints and proximal interphalangeal joints) and of the right wrist. He had a positive test for rheumatoid factor and the diagnosis was rheumatoid arthritis. He was treated with 9 mg of budesonide per day and at follow-up 4 weeks later his disease was under control as can be seen from the data in Table 6. After another 4 weeks his condition had further improved and he was able to return to work.

TABLE 6

| Test | Before | After |
|---|---|---|
| Morning stiffness/min | 120 | 60 |
| Joint arthritic index | 64 | 0 |
| Ritchie index | 8 | 5 |

EXAMPLE 7

A 73 year old woman had suffered from joint swelling and joint pains for about 5 months. At admittance she had symmetric swelling of finger joints, both knees and left ankle. She was on treatment with diclofenac. The rheumatoid factor test was positive and the diagnosis was rheumatoid arthritis. Diclofenac treatment was stopped and she was given 9 mg of budesonide per day. At follow up three weeks later her condition was strikingly improved as can be seen from Table 7.

TABLE 7

| Test | Before | After |
|---|---|---|
| Morning stiffness/min | 210 | 15 |
| Joint arthritic index | 112 | 15 |
| Ritchie index | 19 | 5 |
| Joint pains: at rest/in motion | 10/5 | 0/0 |

EXAMPLE 8

A 73 year old man had for 2 months suffered from rapidly progressive inflammations of the finger joints of both hands (metacarpophalangeal joints, proximal interphalangeal joints) and the wrists. The diagnosis was rheumatoid arthritis. After administration of 9 mg of budesonide once a day he started to feel better after 14 days and at the first clinical follow-up three weeks after start of budesonide treatment his condition had begun to normalise (see the data for the joint arthritic index and Ritchie index in Table 8). At a second follow-up three weeks later the condition was further improved both by clinical and laboratory measurements (see the joint pain data in Table 8).

TABLE 8

| Test | Before | After |
|---|---|---|
| Joint arthritic index | 90 | 0 |
| Ritchie index | 16 | 2 |
| Joint pains: at rest/in motion | 7/7 | 1/1 |

What is claimed is:

1. A method for treating joint inflammation in a patient, the method comprising:
   identifying a patient in need of treatment for joint inflammation; and
   orally or rectally administering to the patient a glucocorticoid substance selected from the group consisting of budesonide, rofleponide, beclomethasone dipropionate, beclomethasone monopropionate, ciclesonide, tipredane, flunisolide, triamcinolone acetonide, and fluticasone propionate, wherein said glucocorticoid substance is released in tie lower part of the small intestine or the upper part of the large intestine, and wherein said glucocorticoid substance is administered in an amount that is therapeutically effective for the non-topical treatment of joint inflammation in the patient.

2. The method of claim 1, wherein the inflammation is rheumatoid arthritis.

3. The method of claim 1, wherein the inflammation is a spondyloarthropathy.

4. The method of claim 3, wherein the spondyloarthropathy is selected from the group consisting of sacroiliitis, reactive arthritides, and psoriatic arthropathy.

5. The method of claim 3, wherein the spondyloarthropathy is ankylosing spondylitis.

6. The method of claim 1, wherein the inflammation is a synovial inflammation.

7. The method of claim 1, wherein the inflammation is an extrasynovial inflammation.

8. The method of claim 1, wherein the inflammation is a peripheral oligoarthritis, a tendonitis, an HLA-B27-associated reactive arthritis, or a joint inflammation associated with an intestinal inflammation.

9. The method of claim 1, wherein the glucocorticoid substance is beclomethasone dipropionate.

10. The method of claim 1, wherein the glucocorticoid substance is budesonide.

11. The method of claim 1, wherein the glucocorticoid substance is rofleponide.

12. The method of claim 1, wherein the glucocorticoid substance is administered in the form of a tablet, a pill, a capsule, a syrup, a powder, a granule, an enema, or a suppository.

13. The method of claim 1, wherein the glucocorticoid substance is administered at a daily dosage of from 0.1 to 40 mg.

14. The method of claim 13, wherein the daily dosage is administered in a single dose or in from two to four divided doses.

15. The method of claim 1, wherein orally administering comprises administering oesophageally.

* * * * *